US00PP34279P2

(12) United States Plant Patent
Hansen

(10) Patent No.: US PP34,279 P2
(45) Date of Patent: May 31, 2022

(54) ***HIBISCUS* PLANT NAMED 'INNER GLOW'**

(50) Latin Name: ***Hibiscus* hybrid (L.)**
Varietal Denomination: Inner Glow

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,081

(22) Filed: Feb. 1, 2022

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Annette H Para

(57) ABSTRACT

A new and distinct cultivar of winter-hardy, herbaceous, perennial, hybrid *Hibiscus* plant named 'Inner Glow' comprising an upright, dense, mound habit of multiple, well-branched, mostly-upright basal stems producing flowers in the upper one-third to one-half of the plant for at least six weeks beginning late July to early August. Flowers have petals that are slightly cupped and slightly puckered and folded, of rich rose-pink with shiny moderate-red eye, a pale lavender-purple hallow center and a deep red and white striped column displaying yellow-colored pollen. The foliage is mainly tri-lobed with olive green and moderate burgundy color blushing. The new plant is useful in the landscape as a specimen plant or en masse.

1 Drawing Sheet

Botanical classification: *Hibiscus* hybrid (L.).
Variety denomination: 'Inner Glow'.

STATEMENT REGARDING PRIOR DISCLOSURES UNDER 37 CFR 1.77(B)(6)

The first publically released non-enabling description was a photograph and brief description of the new plant first on Feb. 1, 2021 when it was listed on a website operated by Walters Gardens, Inc. Subsequently, the new plant had a non-enabling description and photograph in the "Walters Gardens 2021-2022 Catalog" first released on May 21, 2021. The first disclosure, in the form of a sale, was made by Walters Gardens, Inc. on Mar. 29, 2021 to Bachman's Wholesale Nursery followed by sales to Legacy Gardens. Walters Gardens, Inc. obtained the new plant and all information relating thereto, from the inventor. No plants of *Hibiscus* 'Inner Glow' have been sold, in this country or anywhere in the world, nor has any disclosure of the new plant been made, more than one year prior the filing date of this application, and such sale or disclosure within one year was either derived directly or indirectly from the inventor and would be 35 U.S.C § 102(b) exceptions.

BACKGROUND AND ORIGIN OF THE PLANT

The present invention relates to the new and distinct hardy, herbaceous, *Hibiscus* plant, *Hibiscus* 'Inner Glow' hybridized under direction of the inventor on Aug. 30, 2016 at a wholesale perennial nursery in Zeeland, Mich. The new plant is a self-pollination of 'Evening Rose' U.S. Plant Pat. No. 33,366. Into the trial process the new plant was assigned the breeder code labeled 16-33-1. The parent has a complex mixture of species, comprising the species: *moscheutos* and *coccineus*.

*Hibiscus* 'Inner Glow' was first asexually propagated in late summer of 2018 by sterile shoot-tip tissue culture and later by greenhouse shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Inner Glow' differs from its parents as well as all other hardy herbaceous *Hibiscus* known to the applicant in many traits. The most similar *Hibiscus* known to the applicant are 'Tie Dye' U.S. Plant Pat. No. 24,078, 'Airbrush Effect' U.S. Plant Pat. No. 29,295, and 'Spinderella' U.S. Plant Pat. No. 33,309.

'Tie Dye' is taller and more upright in habit, the foliage lacks the burgundy coloration, and the inner flower portion surrounding the eye is nearly white. 'Airbrush Effect' has foliage that is dark green, and the flowers are vibrant pink with salmon tones that appear speckled in greater concentration toward the apex. 'Spinderella' has a taller and broader habit, the foliage is ovate and deep-green colored, and the flowers have a darker pink leading edge and the apex of the petals with the overlapped edge of nearly white.

'Evening Rose' has flowers of vivid purplish-red coloration, without the lighter portion surrounding the eye.

*Hibiscus* 'Inner Glow' is a unique winter-hardy herbaceous *Hibiscus* with the following combined traits:

1. Winter-hardy compact perennial with upright habit of multiple, well-branched, basal stems;
2. Many flat rotate flowers;
3. Flowers produced for about five to six weeks beginning mid-summer;
4. Flower petals of rich rose-pink with deep red and white striped column displaying yellow pollen;

5. Flower is slightly cupped with slight puckering and folding in petals giving extra strength and support to flower;
6. Flower has a moderate-red shiny eye zone surrounded by pale lavender-purple halo center;
7. Foliage is mainly tri-lobed, olive green with moderate burgundy blushing.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
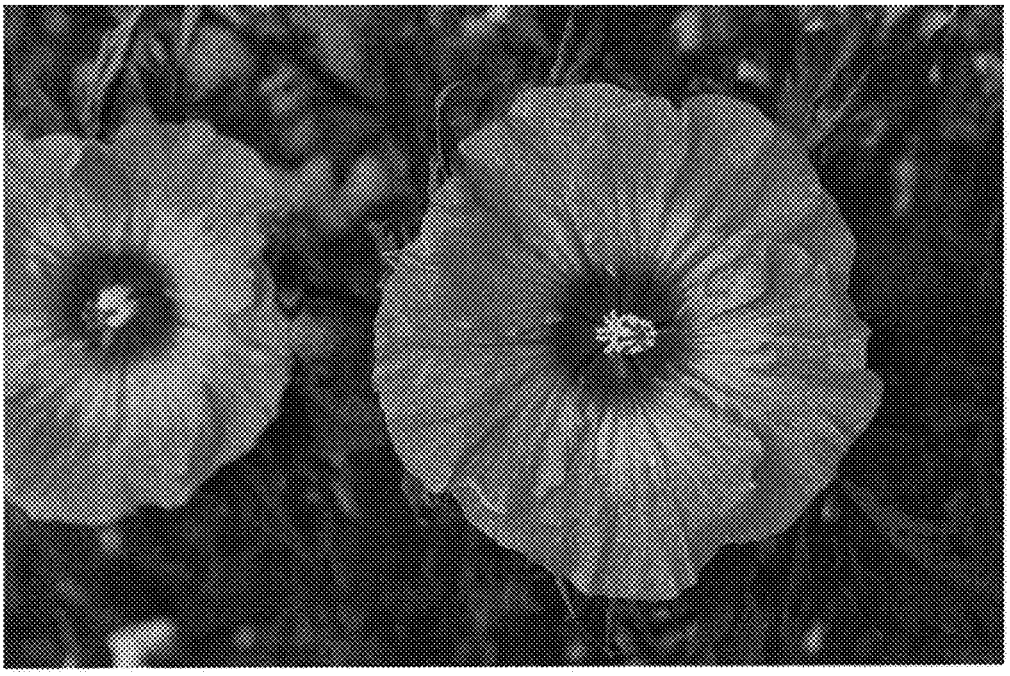
FIG. 1 shows a close-up of the flower and bud.
Figure 2:
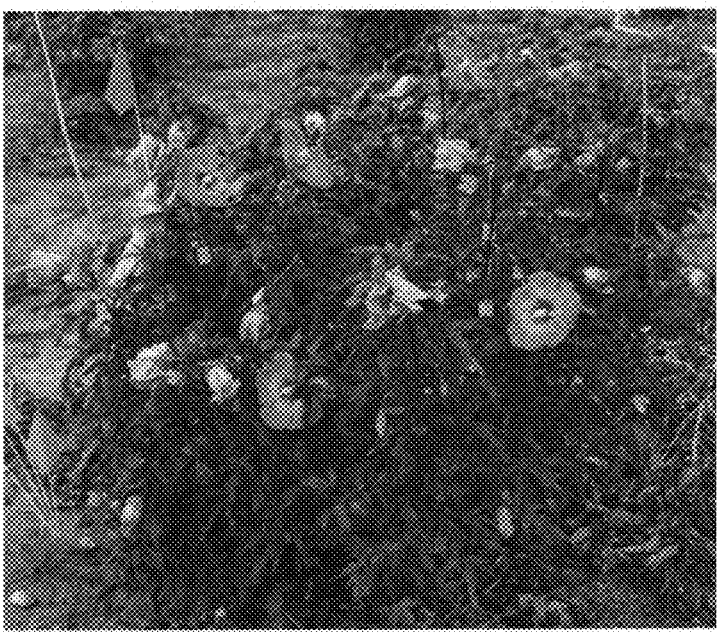
FIG. 2 shows a four-year-old plant in full flower in a trial garden.

The following descriptions and color references are based on the 2001 edition of The Royal Horticultural Society Colour Chart except where common dictionary terms are used. The new plant, *Hibiscus* 'Inner Glow', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The parent is 'Evening Rose';

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.2 cm diameter, fleshy.

*Root color*.—Creamy yellow, nearest RHS 161D depending on soil type.

*Crop time*.—Under normal summer growing conditions 12 to 16 weeks to flower in a four-liter container from cutting; plant vigor very good.

Plant description:

*Plant habit*.—Winter-hardy herbaceous perennial with about 24 thick, mostly upright, heavily-branched stems producing an upright mound to about 110 cm tall and about 120 cm wide.

*Stem*.—Cylindrical, glabrous, glaucous; to about 105 cm tall and about 2.2 cm diameter at base, average about 95 cm tall and about 1.5 cm diameter at base.

*Stem color*.—Distally nearest RHS N186C, proximally between RHS 147C and RHS 138C.

*Lateral branches*.—To 15 per stem, average about 5 per stem; emerging at about 45° angle from main stem; cylindrical; glabrous; glaucous; with up to 10 flowers per branch; to about 32 cm long and 5.0 mm diameter at base, smaller distally.

*Lateral branch color*.—Distally nearest RHS N186C, proximally nearest RHS 138B.

*Internode*.—About 20 to 25 nodes per stem below individual flowers; average internode length about 4.2 cm on unpinched plant.

*Internode color*.—Indistinguishable in color from surrounding stem.

Foliage description: Tri-lobed to penta-lobed; lobes dissected to nearly three-quarters of the way to petiole; alternate; apex narrowly acute; base rounded to nearly cordate; margin coarsely and irregularly dentate; micro [puberulent adaxial and abaxial glabrous; adaxial surface slightly lustrous when expanding and matte when mature, abaxial surface matte; leaf blades to about 45.5 cm long and about 12.2 cm across, average blade size about 14 cm long and about 9 cm across; no fragrance detected;

*Foliage color*.—Young expanding leaves adaxial variable with strong anthocyanin between RHS N186B and RHS N186A and also regions toward base between RHS 138A and RHS 137C, abaxial expanding nearest blend between RHS 147C and RHS N138D with irregular light blushing typically around leaf margins nearest RHS 187B; mature leaves — adaxial variable between RHS N187A and RHS 187A mottled with between RHS 146B and RHS 144A, abaxial between RHS 147B and RHS 146D with light anthocyanin blushing distally nearest RHS 187A.

*Veins*.—Palmate; lustrous; glabrous; costate on abaxial.

*Vein color*.—Young adaxial veins nearest RHS 187A with midrib nearest RHS, abaxial veins between RHS 146C and RHS 145B with moderate pigmenting of nearest RHS 187C; mature adaxial midrib nearest RHS 187A, abaxial nearest RHS 145B with moderate to strong anthocyanin pigmenting nearest RHS 187C.

*Petioles*.—Mostly cylindrical; proximally slightly applanate on adaxial surface near base; glaucous; glabrous; to about 6.8 cm long and 5.0 mm diameter at base, average size about 5.6 cm long and 3.5 nun wide at base.

*Petiole color*.—Adaxial nearest RHS N186C abaxial and nearest RHS 146C variably blushed with nearest RHS N186C.

Flower description: Complete; solitary; perfect; actinomorphic; mostly outwardly facing; rotate; lasting up to two days on plant; to about 16.0 cm across and slightly cupped petals and 6.5 cm deep with column extending 38 mm long, flower size decreasing distally;

Buds one day prior to anthesis: Ellipsoidal with bluntly rounded apex and bluntly rounded base; with petal apices not tightly folded together; sepals adpressed to petals; about 4.7 cm long and about 3.3 cm diameter in middle;

Bud color one day prior to anthesis: Exposed petal color nearest RHS 60A and sepals nearest RHS 146C with strong anthocyanin blush on veins and sepal center nearest RHS 187B;

Epicalyx: Typically 10 to 12 per flower; linear; entire; with margin micro-ciliolate; glabrous adaxial and micro-puberulent abaxial; dull surface adaxial and abaxial; narrowly acute apex and truncate base, distally arcuate toward center; to about 19.0 mm long and to about 2.5 mm wide at base;

Epicalyx color: Adaxial nearest RHS 146B, abaxial between RHS 138A and RHS 146B with moderate to heavy blushing of nearest RHS N186C in distal abaxial surface;

Calyx: Star-shaped hypanthium; campanulate; 18.0 mm deep and 55.0 mm across;

Sepals: Five, fused in basal 1.5 cm and free in distal 1.9 cm; acute apex; glabrous adaxial and abaxial; margin entire, edentate; adaxial and abaxial surfaces matte; individually about 34.0 mm long, about 19.0 mm wide at fusion;

Sepal color: Adaxial between RHS 146C and RHS 147C, midrib nearest RHS 145C and primary veins nearest RHS 146B; abaxial nearest RHS 146B heavily blushed around veins with anthocyanin nearest RHS 187B;

Inflorescence: Up to 40 total solitary flowers per main stem without pinching, 18 on the upper unbranched portion and 22 in the lower branched portions;

Flowering season: Effective for five to six weeks beginning late July to early August depending on weather;

Flower fragrance: None detectable;

Petals: Five; glabrous adaxial and abaxial, lustrous eye; adnate to the androecium to form a column, imbricate to about 45% overlapping at widest part (petals overlapping 45% to the petals on either side); palmately veined, primary veins impressed on adaxial and slightly costate abaxial; surface slightly dimpled with irregular folding; rounded with distinct claw and limb; margins: entire, edentate; apex rounded; base short claw-like;

Petal size: Average about 9.5 cm across and about 9.5 cm long, claw base about 8.5 mm across, smaller in later part of flowering season;

Petal color: Adaxial distal 35.0 mm wide region nearest RHS 67B with veins nearest RHS 64A, 5.0 mm of internal center eye nearest RHS 53A, region between 5.0 mm and 17.0 mm from center nearest RHS 59A, central 25.0 mm wide between RHS N66D and RHS 76C with veins radiating through the middle of nearest RHS 59A proximally and distally becoming nearest RHS 64B; abaxial basal 20 mm of eye RHS NN155D, distal 8.0 mm of eye a blend between RHS 67C and RHS 67B, distally transitioning from between RHS N66D and RHS 76C in the center portion to nearest RHS 67B along the distal margin;

Flower lastingness: One to up to two days in cooler conditions;

Gynoecium: Single; partially enclosed in column; 50.0 mm long;

*Column*.—Lustrous and glabrous, fringed distally with acute lobe apices; about 31.0 mm long and about 10.0 mm across at base; with pistil exserted about 13.0 mm.

*Column color*.—Proximally between RHS 53A and RHS 53B, distally striated with between RHS 53B and NN155D, with apex nearest RHS 53B.

*Style*.—Micro-puberulent in region exserted above column, glabrous below in region contained in column; about 37.0 mm long and 2.0 mm diameter at base, penta-furcate in about distal 10.0 mm; branch diameter about 1.2 mm; color nearest RHS NN155B, distally transitioning to between RHS 60C and RHS 61B.

*Stigma*.—Typically five; flattened globose, puberulent, about 2.0 mm in diameter and 1.0 mm tall; color nearest RHS 59C.

*Ovary*.—Superior; conical; broadly acute apex; truncate base; longitudinally fluted; to about 11.0 mm across at base and about 9.0 mm tall; color nearest RHS 150D.

Androecium: On column;

*Filaments*.—Numerous, about 120; about 3.5 mm long and about 0.2 mm diameter; attached along nearly the entire length of column; color individually nearest RHS 63D proximally and nearest RHS N155D distally.

*Anthers*.—Flattened reniform; dorsifixed; about 2.0 mm long and 2.0 mm across and about 1.0 mm thick; color between RHS 11C and RHS 11B.

*Pollen*.—Abundant, globose, less than 0.1 mm long; color nearest RHS 13C.

Pedicel: Cylindrical; glabrous; lustrous; lustrous; upright; arcuate; size to about 4.5 mm diameter distally and 3.0 mm diameter proximally, length from abscission point to stem node to about 40.0 mm long; longer on earlier flowers and decreasing on later distal flowers;

Pedicel color: Distal portion nearest RHS 146B with moderate anthocyanin blush of nearest RHS 187B, proximal portion below abscission nearest RHS 146B with moderate to heavy anthocyanin blush of nearest RHS 187B;

Peduncle: Cylindrical, glabrous, glaucous; to about 110.0 cm long and 2.2 cm diameter at base, average about 95.0 cm long and 1.5 cm diameter at base; flowering in the distal one-third to one-half; with up to 15 branches that are up to 32 cm long;

Peduncle color: Distally nearest RHS N186C where exposed to high light, and nearest RHS 146D where protected from high light exposure, proximally between RHS 147C and RHS 138C;

Fruit: Globose to ellipsoidal, penta-loculicidal capsule; pubescent along inner septa with hairs of nearest RHS 158A to about 4.0 mm long, glabrous outside; cuspidate apex and flattened base; about 19.0 mm long and 18.0 mm diameter; color nearest RHS 200A when mature;

Seed: About 30 to 40 seeds per pod; minutely floccose; globose; about 3.0 mm in diameter; color between RHS N199C and RHS N199B;

Resistance: *Hibiscus* 'Inner Glow' has not displayed any pest and disease resistance or susceptibility beyond that typical of hardy perennial *Hibiscus*.

Growing conditions: The plant grows best in full-sun with plenty of moisture.

Winter hardiness: At least from USDA zone 4 through 9, and other disease resistance is typical of that of other hardy *Hibiscus* cultivars.

I claim:

1. A new cultivar of hardy herbaceous perennial *Hibiscus* plant named 'Inner Glow' as herein illustrated and described.

* * * * *